United States Patent [19]

Lau

[11] Patent Number: 4,814,472

[45] Date of Patent: * Mar. 21, 1989

[54] DIETHYNYLATED DIPHENYL HEXAFLUOROPROPANES

[75] Inventor: Kreisler S. Y. Lau, Alhambra, Calif.

[73] Assignee: Hughes Aircraft Company, Los Angeles, Calif.

[*] Notice: The portion of the term of this patent subsequent to Feb. 15, 2000 has been disclaimed.

[21] Appl. No.: 466,271

[22] Filed: Feb. 14, 1985

Related U.S. Application Data

[63] Continuation-in-part of Ser. No. 318,716, Nov. 6, 1981, Pat. No. 4,374,291.

[51] Int. Cl.$^4$ .......................... C07F 7/08; C07F 20/22; C07F 33/26; C07F 57/38
[52] U.S. Cl. .................................... 556/431; 546/275; 549/80; 549/472; 560/81; 562/488; 564/155; 568/660; 568/809; 570/128
[58] Field of Search ................. 570/128, 129; 556/431; 560/81; 562/488; 564/155; 568/660, 809; 546/275; 549/80, 472

[56] References Cited

U.S. PATENT DOCUMENTS 4,374,291 2/1983 Lau ...................................... 585/320

OTHER PUBLICATIONS

Hanley, "The Condensed Chemical Dictionary" pp. 90 and 972, 10th ed. 1981).
"Websters Third New International Dictionary", unabridged, pp. 116 and 125, 1963.

Primary Examiner—J. E. Evans
Attorney, Agent, or Firm—M. E. Lachman; A. W. Karambelas

[57] ABSTRACT

There are disclosed diethynylated diphenyl hexafluoropropane compounds, which are suitable for forming copolymers and carbon-carbon composites. These compounds are prepared in high yields by first providing a dihalogenated diphenyl hexafluoropropane compound, coupling the dihalogenated compound with ethynyltrimethylsilane in the presence of an organometallic catalyst to form a silylated ethynyl terminated diphenyl substituted compound and subsequently desilylating the compound to form the desired diethynylated diphenyl hexafluoropropane compound.

6 Claims, 2 Drawing Sheets

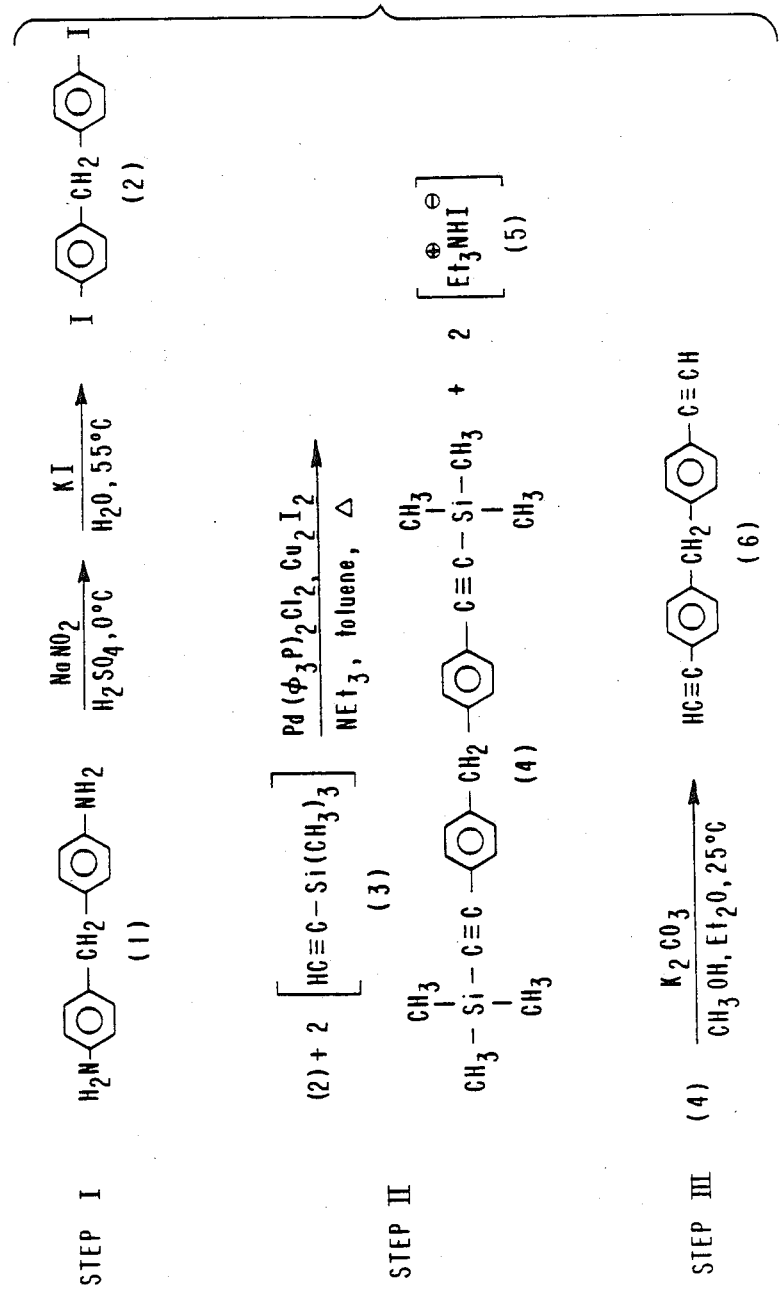

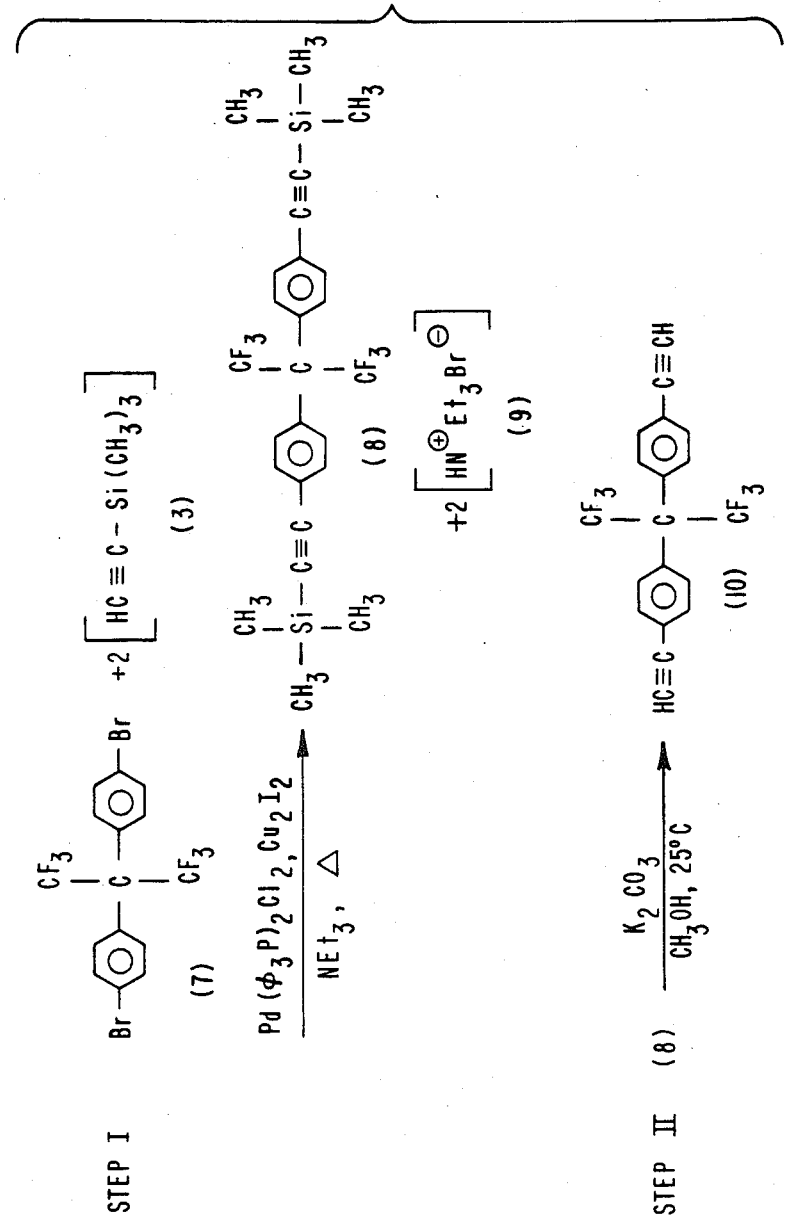

DIETHYNYLATED DIPHENYL HEXAFLUOROPROPANES

CROSS-REFERENCE TO RELATED APPLICATIONS

This application is a Continuation-in-Part of U.S. application Ser. No. 318,716 filed Nov. 6, 1981 by Applicant for Synthesis of Bis(Ethynylphenyl) Compounds, now U.S. Pat. No. 4,374,291 issued Feb. 15, 1983.

TECHNICAL FIELD

This invention relates, generally, to the synthesis of ethynylphenyl and ethynylphenylhexafluoropropane compounds, and more particularly to the synthesis of 4,4'-diethynyldiphenylmethane and 2,2-bis(4-ethynylphenyl)hexafluoropropane.

This application is related to U.S. Pat. No. 4,465,833 by Applicant and another for "Ethynylated Aromatic Compounds and Process for Making Same". It differs from U.S. Pat. No. 4,465,833 in that this application and the parent application thereof disclose a process for preparing bis(ethynylphenyl) compounds, whereas U.S. Pat. No. 4,465,833 discloses ethynylated aromatic compounds having base sensitive substituents. Both applications are commonly assigned to Hughes Aircraft Company of Culver City, Calif.

BACKGROUND OF THE INVENTION

1. Field of the Invention

Bis(ethynylphenyl) compounds, also known as ethynylated bis-aryl derivatives, are important intermediates in the synthesis of thermally stable resins for use in high-temperature structural composites and high-char yielding structure matrices, such as carbon-carbon composites. These materials are used in the fabrication of reentry missile nose cones, leading edges, rocket nozzles, and other structural applications requiring high structural strength and high thermal stability. The invention disclosed below describes a simplified process for preparing these intermediates in high yields that may readily be adapted to large-scale synthesis operations.

2. Description of the Prior Art

Classical methods for the synthesis of terminal aryl acetylene in general involve manipulation of preformed two-carbon side chains and include methods such as the Vilsmeier method, the halogenation dehydrohalogenation sequence of vinyl aromatics and aromatic ketones and the dehydrohalogenation of $\beta,\beta$-dihalo olefins. Methods that deviate from the classical approach have utilized the decomposition of preconstructed heterocycles. More recently, acetylenic substituents have been introduced onto aromatic nuclei by the Stephens-Castro coupling reaction. Since this reaction requires a stoichiometric quantity of an acetylenic copper reagent, prior preparation of such a reagent is needed, which consumes time, materials and energy. Also, the Stephens-Castro reaction requires the use of end-protecting groups such acetals, ketones, ketals, hydroxymethyl, tetrahydropyran-protected hydroxymethyl, dimethylcarbinol, or ethyl vinyl ether-protected carbinol. The removal of these groups often requires several steps and/or strongly alkaline media which tend to attack either the acetylenic linkage of the ethynyl group or any electron-withdrawing substituents on the aromatic nucleus. Therefore, there is a need for a simple process for preparing bis(ethynylphenyl) compounds in good yield that is suitable for large-scale synthesis operations. In particular, there is a need for a process for preparing 4,4'-diethynyldiphenylmethane and 2,2-bis(4-ethynylphenyl)hexafluoropropane in good yield.

SUMMARY OF THE INVENTION

In seeking to provide an improved process for the synthesis of 4,4'-diethynyldiphenylmethane in high yields that is suitable for large-scale synthesis operations, while avoiding the disadvantages of the prior art and at the same time retaining the advantages thereof, it has been discovered that bis(ethynylphenyl) compounds may be prepared in high yields by first providing a dihalogenated diphenyl compound, coupling the dihalogenated compound with ethynyltrimethylsilane in the presence of an organometallic catalyst to form a silylated ethynyl terminated diphenyl substituted compound and subsequently desilylating the compound to form the desired bis(ethynylphenyl) compound.

In experimentation with this process, it has been discovered that the process can be used to prepare the novel compound 2,2-bis(4-ethynylphenyl)hexafluoropropane as a final product and the novel compound 2,2-bis(4-trimethylsilylethynylphenyl)hexafluoropropane as an intermediate. Similarly, this process can also be used to prepare another novel compound, namely, 2,2-bis(3-ethynylphenyl)hexafluoropropane by means of another novel intermediate, 2,2-bis(3-trimethylsilylethynylphenyl)hexafluoropropane.

Furthermore, the organometallic-catalyzed coupling reaction process between dihalogenated diphenyl compounds and ethynyltrimethylsilane can be applied to the synthesis of other alkylylated or arylated diethynyl diphenyl compounds.

The process of this invention begins, for convenience, with the diazotization of a dianiline compound having the structure

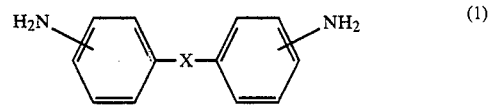

(1)

where X is a single bond, CO, $SO_2$, $NC_6H_5$, S, $Si(CH_3)_2$, $POCH_3$, $POC_6H_5$, $(CH_2)_n$, or $C(CF_nH_{3-n})_2$, where n is 0, 1, 2 or 3, to form an intermediate dihalodiphenyl compound. Alternatively, it may begin with the provision of the dihalodiphenyl compound obtained through another process as will be described herein which is especially appropriate in the case of dihalogenated 2,2-diphenylhexafluoropropanes. The diazotization of the above dianiline is accomplished by treating it with $NaNO_2$ and a selected inorganic halide in a strong acid, as is well-known. The dihalodiphenyl intermediate is then reacted with ethynyltrimethylsilane (in a coupling reaction) in an amine solvent in the presence of a catalytic mixture formed from an organometallic complex and a ligand, thereby forming a bis(trimethylsilyl)ethynylated derivative. The bis(trimethylsilyl)ethynyl derivative is then treated with a weak base in an ether-alcohol solvent to thereby form the desired diethynyl compound.

It is therefore one purpose of this invention to provide a generalized process for synthesizing bis(ethynylphenyl) compounds in high yields.

Another purpose of this invention is the provision of the compounds 2,2-bis(4-ethynylphenyl)hexafluoropropane and its isomer 2,2-bis(3-ethynylphenyl)hexafluoropropane and a process for synthesizing such compounds.

A further purpose of this invention is to provide an improved process for synthesizing 4,4'-diethynyldiphenylmethane in high yields.

A still further purpose of this invention is to provide compounds for use in the synthesis of oligomers and resins suitable for use in the fabrication of high strength, high thermal stability compounds.

That I have accomplished these purposes, and others, will be apparent upon reference to the following drawings and detailed description of the invention.

BRIEF DESCRIPTION OF THE DRAWINGS

FIG. 1 is a schematic of a reaction process for producing 4,4'-diethynyldiphenylmethane; and FIG. 2 is a schematic of a reaction process for producing 2,2-bis(4-ethynylphenyl)hexafluoropropane with 2,2-bis(4-trimethylsilylethynylphenyl)hexafluoropropane as an intermediate.

DETAILED DESCRIPTION OF THE INVENTION

It has been discovered that dihalogenated diphenyl compounds can be coupled with ethynyltrimethylsilane in the presence of an organometallic catalyst to produce a silylated ethynyldiphenyl compound that may be subsequently desilylated to quantitatively yield a bis(ethynylphenyl) compound. The process of this invention may begin with the provision of the dihalo diphenyl compound from commercial sources or by synthesis described in Example IV below, or it may begin with a diamino diphenyl (or dianiline) compound whose structure is:

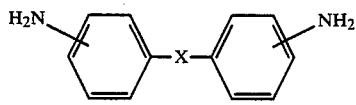

(1)

where X is a single bond, CO, $SO_2$, $NC_6H_5$, S, $Si(CH_3)_2$, $POCH_3$, $POC_6H_5$, $(CH_2)_n$, or $C(CF_nH_{3-n})_2$, where n is 0, 1, 2 or 3. These compounds are known in the art and some of them can be obtained from suppliers such as Aldrich Chemicals of Milwaukee, Wis.; Eastman Chemical Co. of Rochester, N.Y.; and Tridom Chemical Inc. of Hauppauge, N.Y.; others can be synthesized by available procedures that are known in the art. For practical applications, meta and/or para-substituted dianilines are selected. Ortho-substituted are not practical in that polymerization with ortho-substituted ethynyl groups is difficult.

The diaminophenyl compounds of (1) are diazotized to form aromatic halides whose structures are:

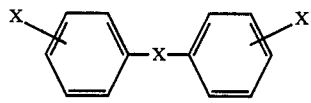

(2)

where X is I or Br and X is as defined above, by forming a slurry of the aminophenyl compound in a strong acid (in excess) with $NaNO_2$ (in a slight excess). As is well-known in the art, the temperature of the slurry is held below 5° C. for safety considerations. An inorganic halide such as KI, NaI or $Cu_2Br_2$ is subsequently added and the mixture is warmed to initiate the reaction. Acids such as HCl, $H_2SO_4$ and HBr are suitable. The strength of acid required is approximately inversely proportional to the strength of the basicity of the dianiline compound utilized.

Having obtained an aromatic halide of structure (2) in high purity, one then proceeds to couple the halide with ethynyltrimethylsilane (thereby introducing acetylenic moieties onto the molecule) by mixing the two compounds in deaerated toluene or benzene and any convenient amine solvent such as triethylamine, tripropylamine, or pyridine and warming the mixture in the presence of an organopalladium complex such as dichlorobis-(triphenylphosphine)palladium[II], a ligand and an inorganic reducing agent to form a bis(trimethylsilylethynyl)diphenyl derivative. When dichlorobis(triphenylphosphine)palladium[II] is employed, it is necessary to add a reducing agent such as $Cu_2I_2$ to ensure quantitative yields. A catalytic mixture containing palladium acetate is also suitable for this coupling reaction. Stabilizing ligands such as triphenylphosphine, tris(o-tolyl)phosphine, triphenylarsine and triphenylstibine are suitable, although triphenylphosphine is most commonly used because of its availability and low cost. After workup and distillation, quantitative yields of the end-protected bis(trimethylsilylethynyl) diphenyl derivative are formed for subsequent conversion to the bis(ethynylphenyl) derivative.

The final step of this process is accomplished by forming a solution of the end-protected diphenyl derivative in an anhydrous low boiling alcoholic solvent and subsequently adding a weak base, such as anhydrous potassium carbonate, with stirring under an inert atmosphere at room temperature. Short chain aliphatic alcohols such as methanol, ethanol, iso-propanol, and tert-butyl alcohol are suitable. However, in some instances, it may be necessary to form an alcohol-ether mixture to increase the solubility of the ethynylated derivative in the solvent.

Inasmuch as the removal of the end-protecting groups, or desilylation, is accomplished in the presence of a weak base in contrast to the prior art practice of utilizing a strong base, base-sensitive substituents on the molecule are tolerated.

According to the present invention, compounds can be synthesized having the general structure

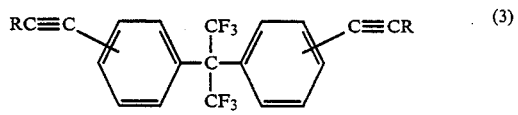

(3)

where $-C\equiv CR$ is in either the meta or para position and where R is selected from the group consisting of: (1) H; (2) $C_nH_{2n+1}$, where n=1 to 10; (3) $C(CH_3)_2OR'$; (4) $CO_2R''$; (5) groups selected from the group consisting of naphthyl, anthryl, phenanthryl, pyridinyl furanyl, thiophenyl, pyrenyl, biphenylyl; and $C_6H_4$-R' (6) CONR"H or CONR"$_2$, and (7) trimethylsilyl, where R' is H or $C_nH_{2n+1}$ where n=1 to 10 and R" is the same as R' or a group selected from the group consisting of $C_6H_5$, naphthyl, anthryl, phenanthryl, 2-pyridinyl, and $C_6H_4$-R'.

Examples of such compounds are:

2,2-bis(3- or 4-methylethynylphenyl)hexafluoropropane;

2,2-bis(3- or 4-decylethynylphenyl)hexafluoropropane;

2,2-bis[3- or 4-(3-hydroxy-3-methyl-1-butynyl)phenyl]hexafluoropropane;

2,2-bis[3- or 4-(carboxyethynyl)phenyl]hexafluoropropane;

aryl esters of 2,2-bis[3- or 4-(carboxyethynyl)phenyl]hexafluoropropane;

alkyl esters of 2,2-bis[3- or 4-(carboxyethynyl)phenyl]hexafluoropropane;

amide derivatives of 2,2-bis[3- or 4-(carboxyethynyl)phenyl]hexafluoropropane;

2,2-bis[3- or 4-(phenylethynyl)phenyl]hexafluoropropane;

2,2-bis[3- or 4-(o- or m- or p-tolylethynyl)phenyl]hexafluoropropane;

2,2-bis[3- or 4-($\beta$-naphthylethynyl)phenyl]hexafluoropropane;

2,2-bis[3- or 4-(9-anthrylethynyl)phenyl]hexafluoropropane;

2,2-bis[3- or 4-(1-pyrenylethynyl)phenyl]hexafluoropropane;

2,2-bis[3- or 4-(2-pyridinylethynyl)phenyl]hexafluoropropane;

2,2-bis[3- or 4-(3-pyridinylethynyl)phenyl]hexafluoropropane;

2,2-bis[3- or 4-(4-pyridinylethynyl)phenyl]hexafluoropropane;

2,2-bis[3- or 4-(4-(2'- or 3'- or 4'-biphenylylethynyl)phenyl]hexafluoropropane;

2,2-bis[3- or 4-(2-furanylethynyl)phenyl]hexafluoropropane; and 2,2-bis[3- or 4-(2-thiophenylethynyl)phenyl]hexafluoropropane.

In experimentation with this process, it has been discovered that the process can be used to prepare the novel compounds 2,2-bis(4-ethynylphenyl)hexafluoropropane and 2,2-bis-(3-ethynylphenyl)hexafluoropropane as final products and the novel intermediate compounds 2,2-bis(4-trimethylsilylethynylphenyl)hexafluoropropane and 2,2-bis(3-trimethylsilylethynylphenyl)hexafluoropropane.

Examples of processes for the production of some of the novel compounds, novel intermediates and other intermediates according to this invention are described below in connection with FIGS. 1 and 2. Specific examples of these processes and other specific examples of the invention are also described below.

Examples I through III describe the preparation of 4,4'-diethynyldiphenylmethane. Examples IV through VI describe the preparation of 2,2-bis(4-ethynylphenyl)hexafluoropropane with 2,2-bis(4-trimethylsilylethynylphenyl)hexafluoropropane as an intermediate. Examples VII through IX describe the preparation of 2,2-bis(3-ethynylphenyl)hexafluoropropane with 2,2-bis(3-trimethylsilylethynylphenyl)hexafluoropropane as an intermediate. Examples X and XI describe, respectively, preparations for 2,2-bis[4-(3-hydroxy-3-methyl-1-butynyl)phenyl]hexafluoropropane and 2,2-bis(4-phenylethynylphenyl)hexafluoropropane, which are other compounds that can be produced according to the invention. The compound numbers in the Examples refer to those on the drawings.

EXAMPLE I

Preparation of 4,4'-Diiododiphenylmethane

In Step I of FIG. 1, 4,4'-diaminodiphenylmethane [Compound (1)] was diazotized to form 4,4'-diiododiphenylmethane [Compound (2)] by forming a slurry of 17.0 g (85.9 moles) of 4,4'-diaminodiphenylmethane in 300 ml concentrated sulfuric acid and stirring at 25° C. until all solid particles dissolved. A dark brown solution was obtained and subsequently cooled to 0°-5° C. while a 30 ml aqueous solution of 17.0 g (0.239 mole) of sodium nitrite was added dropwise. Care was taken not to let the temperature of the mixture rise above 5° C. After the addition of sodium nitrite was completed, the slurry was stirred for 30 minutes at 5° C. and then slowly poured into an aqueous solution of 100 g of potassium iodide in 2 liters of water pre-heated to 55° C. The resulting mixture was stirred for 1 hour at 55° C., cooled to 25° C., mixed with 1 liter of dichloromethane, neutralized with the addition of 50% aqueous sodium hydroxide, and then decolorized with saturated aqueous sodium bisulfite solution. A brown organic phase was obtained which was separated and washed with 500 ml each of 10% aqueous hydrochloric acid, distilled water, saturated aqueous sodium bicarbonate, and then water. After drying over magnesium sulfate and concentrating on a rotary vacuum evaporator, the residual crude oil was purified by column chromatography through silica gel using hexane as eluant to yield a white crystalline solid. The white crystalline solid was identified as 4,4-iiodiphenylmethane [Compound (2)]: 15.0 g (35.7 mmoles, 41.6%); mp 85°-86° C.; IR(KBr) 2950 (weak, sharp CH), 1490, 1400 (strong, sharp, C=C), 1020, 810, 780 cm$^{-1}$ (strong, sharp); NMR(CDCl$_3$) $\delta$ 3.83 (s, 2H, CH$_2$), 6.87 and 7.60 ppm (q, 8H, J$_{AB}$=8.0 Hz, aromatic).

EXAMPLE II

Preparation of Bis(4-trimethylsilylethynylphenyl)methane

In Step II of FIG. 1, 4,4'-diiododiphenylmethane [Compound (2)] was then coupled with ethynyltrimethylsilane [Compound (3)] to form an end-protected bis(4-trimethylsilylethynylphenyl)methane [Compound (4)] by forming a solution comprising 8.40 g (20.0 mmoles) of 4,4'-diiododiphenylmethane and 2.50 g (25.5 mmoles) of ethynyltrimethylsilane in 150 ml of 2:1 triethylamine toluene deaerated with argon. This solution was subsequently treated with a catalyst mixture comprising 50 mg of dichlorobis(triphenylphosphine)palladium[II], 150 mg of triphenylphosphine and 50 mg of copper[I] iodide. The yellow solution thus obtained was stirred and warmed to 80°-90° C. over 1 hour and kept in this temperature range for 4 hours. A copious white precipitate was formed which was filtered off after cooling to 25° C. and diluting with 150 ml of ether. The yield of triethylamine hydroiodide [Compound (5)] was quantitative. The filtrate was concentrated to a thick oil, dissolved in 200 ml of ether and washed with 200 ml each of 10% aqueous hydrochloric acid, water, saturated aqueous sodium bicarbonate, and water again. The ethereal phase was dried over magnesium sulfate and concentrated to an oil which crystallized on standing. The solid was taken up in 100 ml of 1:1 hexane/dichloromethane and filtered through a bed of silica gel. The filtrate was evaporated down to half of the original volume and cooled at −78° C. to precipitate 7.20 g (20.0 mmoles; 100%) of a crystalline solid. Recrystallization from hexane yielded pure, lustrous crystals in 81% recovery: mp 110°–111° C.; IR(KBr) 2790 (strong, sharp, SiCH$_3$), 2160 (strong, sharp, C≡C), 1505 (strong, sharp, C=C), 1250 (strong, sharp, SiCH$_3$) and 840 cm$^{-1}$ (very strong, broad, Si-C bending); NMR(CDCl$_3$) δ 0.28 (s, 18H, SiCH$_3$), 3.92 (s, 2H, CH$_2$), 7.37 and 7.40 ppm (q, 8H, J$_{AB}$=8.0 Hz, aromatic).

Analysis for C$_{23}$H$_{28}$Si$_2$(360.6): Calculated: C,75.49; H,7.83; Si,15.58. Found: C,76 28; H,7.84; Si,15.84.

EXAMPLE III

Preparation of 4,4'-Diethynyldiphenylmethane

In Step III of FIG. 1, a suspension of 1.00 g (2.78 mmoles) of bis(4-trimethylsilylethynylphenyl)methane [Compound (4)] in 50 ml anhydrous deaerated methanol was treated with enough anhydrous ethyl ether to dissolve all solid particles at 25° C. Anhydrous potassium carbonate (300 mg) was added and the mixture was stirred at 25° C. under argon for 16 hours. The solvent was removed and the solid residue was dissolved in 50 ml dichloromethane, treated with 5 g of silica gel and evaporated to dryness. The powder was placed on top of a 40 cm (I.D. 30 mm) column of silica gel (EM Labs, 70–230 mesh) and the column was developed with passage of hexane. A crystalline white solid [Compound (6)] was recovered from the eluate: 0.60 gm (2.78 mmoles, 100%); mp 63°–64° C. After drying at 56° C./0.01 mm Hg inside an Abderhalden apparatus for 2 hours, the mp increased to 65.5°–66.5° C. IR(KBr) 3280 (very strong, sharp, —C≡C—H), 2100 (weak, sharp, —C≡C—) and 1500 cm$^{-1}$ (medium, sharp, C=C); MS (70 eV) m/e 216 (molecular ion); NMR(CDCl$_3$) δ 3.03 (s, 2H, C≡C—H), 3.95(s, 2H, CH$_2$), 7.10 and 7.43 ppm (q, 8H, J$_{AB}$=8.0 Hz, aromatic).

Analysis for C$_{17}$H$_{12}$(216.3): Calculated: C,94.41; H,5.59. Found: C,94.34; H,5.70.

EXAMPLE IV

Preparation of 2,2-Bis(4-bromophenyl)hexafluoropropane 2,2-bis(4-bromophenyl)hexafluoropropane can be prepared using the procedure described in U.S. Pat. No. 4,503,254 entitled "Bis(Halophenyl) Hexafluoropropane and Process for Making the Same".

EXAMPLE V

Preparation of 2,2-Bis(4-trimethylsilylethnylphenyl)hexafluoropropane

To a solution of 9.995 g (21.63 mmoles) of 2,2-bis(4-bromophenyl)hexafluoropropane of FIG. 2 [Compound (7)] in 80 ml of deaerated, anhydrous triethylamine, was added the catalyst system which comprised 40 mg of palladium acetate and 120 mg of triphenylphosphine. The cloudy yellow solution was stirred and heated at 40° C. until all the brown particles dissolved. Ethynyltrimethylsilane [Compound (3)] (4.705 g, 48.01 mmoles) was added and the mixture was rapidly heated to 70° C. over 5 minutes. At 60° C., a clear yellow solution was obtained. At 70° C., precipitation of the white triethylamine hydrobromide [Compound (9)] commenced. The reaction temperature was raised to 85°–90° C. over 10 minutes and maintained at that temperature range for 6 hours. The slurry was then cooled, diluted with 100 ml of ether and filtered. The white solid of triethylamine hydrobromide was washed with more ether and air dried. A virtually quantitative yield was realized.

The filtrate was concentrated, dissolved in 200 ml of ether and washed with 100 ml each of 10% hydrochloric acid, water, saturated sodium bicarbonate and water again. The ethereal phase was dried over magnesium sulfate and concentrated to a brown oil which was purified by column chromatography. The second band travelled down the column was eluted with 1.5 liters of hexane. The eluate was concentrated to a "molasses" consistency. NMR(CDCl$_3$) and IR(film) unequivocally identified the product as 2,2-bis(4-trimethylsilylethynylphenyl)hexafluoropropane [Compound (8)]. Yield 9.10 g (18.3 mmoles, 84.8%).

EXAMPLE VI

Preparation of 2,2-Bis(4-ethynylphenyl)hexafluoropropane

The yellow orange "molasses" obtained from the preparation of 2,2-bis(4-trimethylsilylethynylphenyl)hexafluoropropane was dissolved in 150 ml of anhydrous methanol and stirred with 1g of anhydrous potassium carbonate at 25° C. for 16 hours. Removal of solvent left a solid residue which was dissolved in 200 ml of ether and extracted with 2×200 ml of water. The ethereal fraction was dried over magnesium sulfate and concentrated to a yellow oil. Structure elucidation was made by NMR(CDCl$_3$) and IR(film). Silica gel column chromatography eluting with 1:4 hexane/dichloromethane yielded pure product [Compound (10)].

Analysis for C$_{19}$H$_{10}$F$_6$(352.3): Calculated: C,64.78; H,2.86; F,32.36. Found: C,64.02; H,2.58; F,32.11.

EXAMPLE VII

Preparation of 2,2-Bis(3-aminophenyl)hexafluoropropane 2,2-Diphenylhexafluoropropane (138.4 g, 0.455 mol) was dissolved in 1.4 liters of dichloromethane. Then 550 ml of concentrated sulfuric acid was added and the solution was cooled to 0° C. Fuming nitric acid (90% assay, 191 ml) was added dropwise with good stirring over a 1.5 hr. period maintaining the reaction temperature at 0°–6° C. The mixture was then stirred at ambient temperature for 3 hours and then transferred to a separatory funnel for removal of the lower acid level. The organic phase was washed with 3×500 ml of water and then with 500 ml of 15 sodium hydroxide. The washing was then continued with 5% sodium hydroxide until the aqueous layer was colorless. The organic phase was then washed with 3×500 ml of water, dried over magnesium sulfate, and concentrated to yield 173 g of a viscous yellow oil which solidified upon trituration with methanol. The solid was recrystallized from 1.4 liters of absolute methanol. Two additional recrystallizations from methanol gave analytically pure crystals: mp 118°–119° C.

The dinitro product was converted to 2,2-bis(3-aminophenyl)hexafluoropropane by catalytic hydrogenation. The diamine was purified by sublimation at 5μ pressure and recrystallized from heptane: mp 84.5°–85.5° C. Both NMR and MS were consistent with this structure. IR(KBr) 3480, 3390, 1499, 1457, 1245, 1220, 1190 cm$^{-1}$; NMR(CDCl$_3$) δ 3.61 (m, 4H, NH$_2$) and 6.80 ppm (m, 8H, aromatic).

Analysis for C$_{15}$H$_{12}$F$_6$N$_2$(334.3): Calculated: C,53.90; H,3.62; F,34.10; N,8.38. Found: C,54.00; H,3.62; F,33.94; N,8.29.

EXAMPLE VIII

Preparation of 2,2-Bis(3-bromophenyl)hexafluoropropane

Conversion of 2,2-Bis(3-aminophenyl)hexafluoropropane by the Sandmeyer Reaction 2,2-Bis(3-aminophenyl)hexafluoropropane (6.30 g, 18.9 mmol) was added to a magnetically stirred solution of 10 ml of concentrated sulfuric acid and 100 ml of water in a 1-liter Erlenmeyer flask. The mixture was warmed slightly to obtain a homogeneous solution. A saturated aqueous solution of sodium nitrite (2.60 g, 37.7 mmol) was added in small portions with external cooling so that the internal temperature did not exceed 10° C. The cold mixture was added in portions to a refluxing solution of freshly prepared cuprous bromide (16.3 g, 37.8 mmol) in 150 ml of 48% hydrobromic acid. After completion of addition, the reaction mixture was heated at reflux for 15 minutes, cooled to room temperature, filtered, and extracted three times with 100 ml portions of dichloromethane. The organic layer was washed successively with 100 ml of 5% sodium hydroxide solution and 100 ml of water, dried over magnesium sulfate and concentrated. Distillation of the residual oil at 100°–115° C./0.05 torr gave 6.5 g (75%) of the dibromo compound; IR(neat) 1260, 1215, 1180 cm$^{-1}$ (strong, broad, CF$_3$); NMR(CDCl$_3$) δ 7.33 ppm (bm, aromatic).

Analysis for C$_{15}$H$_8$Br$_2$F$_6$(462.0): Calculated: C,38.99; H,1.74; Br,34.59; F,24.67. Found: C,39.01; H,1.75; Br,34.78; F,24.39.

EXAMPLE IX

Preparation of 2,2-Bis(3-trimethylsilylethynylphenyl)hexafluoropropane and 2,2-Bis(3-ethynylphenyl)hexafluoropropane The synthetic procedure used was identical to the one described herein for 2,2-bis(4-ethynylphenyl)hexafluoropropane with one alteration: instead of 2,2-bis(4-bromophenyl)hexafluoropropane, 2,2-bis(3-bromophenyl)hexafluoropropane was used.

EXAMPLE X

Preparation of 2,2-Bis[4-(3-hydroxy-3-methyl-1-butynyl)phenyl]hexafluoropropane The synthetic procedure used was identical to the one described above for 2,2-bis(4-trimethylsilylethynylphenyl)hexafluoropropane with one alteration: instead of ethynyltrimethylsilane, 2-methyl-3-butyn-2-ol was used.

NMR(CDCl$_3$) and IR(film) unequivocally identified the product as 2,2-bis[4-(3-hydroxy-3-methyl-1-butynyl)phenyl]hexafluoropropane.

EXAMPLE XI

Preparation of 2,2-Bis(4-phenylethynylphenyl)hexafluoropropane

The synthetic procedure used was identical to the one described above for 2,2-bis(4-trimethylsilylethynylphenyl)hexafluoropropane with one alteration: instead of ethynyltrimethylsilane, phenylacetylene was used.

The product after purification by column chromatography was a white crystalline solid with a mp of 92°–92.5° C. NMR(CDCl$_3$) and IR(KBr) unequivocally identified the product as 2,2-bis(4-phenylethynylphenyl)hexafluoropropane.

Analysis for C$_{31}$H$_{18}$F$_6$(504.5): Calculated: C,73.81; H,3.60. Found: C,73.83; H,3.47.

The examples shown above are intended as illustrations only and are not to be construed as a limitation. This invention encompasses variations about the general teachings which are within the skills of those who practice in this art such as the utilization of other organometallic complexes as catalyst, temperature optimizations and the selection of other suitable solvents.

Bis(ethynylphenyl) compounds prepared in accordance with this invention may be used to form copolymers as taught in U.S. Pat. No. 4,098,767 and carbon-carbon composites as described and claimed in U.S. Pat. No. 4,284,834.

It has been found, according to this invention, that the compound 2,2-bis(4-ethynylphenyl)hexafluoropropane possesses alone and in combination with other oligomers and polymers highly advantageous properties due to the large processing temperature range of from about 70° C., where the compound is in a very fluid state, to about 225° C., where the compound will start to cure. The compound can be used as a diluent in enhancing the processibility of oligomers and polymers which otherwise would be difficult to process due to their inherent structural rigidity and high glass transition temperatures.

Blending and copolymerization of 2,2-bis(4-ethynylphenyl)hexafluoropropane with selected acetylene-terminated oligomers such as imides, isoimides, phenylquinoxalines, etc., yields interpenetrating polymer networks that are potential structural materials for high temperature applications. Another application for the compound is as a plasticizer for high molecular weight thermoplastic polymers. Subsequent curing of the plasticized mixture allows a crosslinking network to form, embedding the thermoplastic material.

What is claimed is:

1. A compound whose structure is:

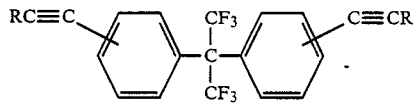

where —C≡CR is in either the meta or para position and where R is selected from the group consisting of:
(1) H;
(2) C$_n$H$_{2n+1}$, where n=1 to 10;
(3) C(CH$_3$)$_2$OR';
(4) CO$_2$R";
(5) a group selected from the group consisting of naphthyl, anthryl, phenanthryl, pyridinyl, furanyl, thiophenyl, pyrenyl, biphenyl, and C$_6$H$_4$-R';
(6) CONR"H or CONR"$_2$; and
(7) trimethylsilyl,
where R' is H or C$_n$H$_{2n+1}$ where n=1 to 10; and R" is the same as R' or a group selected from the group consisting of C$_6$H$_5$, naphthyl, anthryl, phenanthryl, 2-pyridinyl and C$_6$H$_4$-R'.

2. The compound of claim 1 designated 2,2-bis(4-ethynylphenyl)hexafluoropropane.

3. The compound of claim 1 designated 2,2-bis(4-trimethylsilylethynylphenyl)hexafluoropropane.

4. The compound of claim 1 designated 2,2-bis(3-ethynylphenyl)hexafluoropropane.

5. The compound of claim 1 designated 2,2-bis(3-trimethylsilyethynylphenyl)hexafluoropropane.

6. The compound of claim 1 designated 2,2-bis(4-phenylethynylphenyl)hexafluoropropane.

* * * * *